(12) United States Patent
Naughton

(10) Patent No.: US 6,387,068 B1
(45) Date of Patent: *May 14, 2002

(54) SWAB DISPENSER WITH FLUID RESERVOIR

(76) Inventor: John G. Naughton, 174 Linden Dr., Cohasset, MA (US) 02025

(*) Notice: Subject to any disclaimer, the term of this patent is extended or adjusted under 35 U.S.C. 154(b) by 0 days.

This patent is subject to a terminal disclaimer.

(21) Appl. No.: 09/839,183

(22) Filed: Apr. 19, 2001

(51) Int. Cl.[7] .......... A61M 35/00; B65D 83/10; A61B 17/06; A46B 11/00
(52) U.S. Cl. .......... 604/2; 206/210; 206/362; 206/363; 206/438; 401/118; 401/125; 401/129
(58) Field of Search .......... 604/1–3; 206/210, 206/362, 361, 362.3, 363, 438, 63.5, 828; 401/88, 118, 123, 125, 129; 606/162

(56) References Cited

U.S. PATENT DOCUMENTS

| | | |
|---|---|---|
| 3,146,806 A | 9/1964 | Ginsburg |
| 3,881,868 A | 5/1975 | Duke |
| 4,190,153 A | 2/1980 | Olsen |
| 4,446,965 A | 5/1984 | Montiel |
| 4,747,719 A | 5/1988 | Parkin |
| 5,016,651 A | 5/1991 | Stalcup et al. |
| 5,112,297 A | 5/1992 | Stalcup et al. |
| 5,131,536 A | 7/1992 | Wu |
| 5,330,056 A | 7/1994 | de la Rocha |
| 5,378,226 A | 1/1995 | Hanifl et al. |
| 5,709,866 A | 1/1998 | Booras et al. |
| 5,947,986 A | 9/1999 | Lewis |
| 6,186,971 B1 * | 2/2001 | Naughton .......... 604/2 |

* cited by examiner

Primary Examiner—Dennis Ruhl
(74) Attorney, Agent, or Firm—Morse, Altman & Martin

(57) ABSTRACT

A swab dispenser comprising a bin adapted to store swabs, a fluid reservoir, and optionally, a cover. The bin may be compartmentalized. The reservoir ceiling has a depression in its outer surface, an aperture at the low point of the depression, and is optionally removable for cleaning and filling. A membrane covers the aperture. The membrane has an opening that is at least two intersecting slits or a circular hole that allows a swab to be inserted into the reservoir by temporarily deforming the membrane. Preferably, the floor of the reservoir is concave with the low point directly below the aperture. Alternatively, the bin and reservoir are separable so one may be replaced without having to discard the other.

18 Claims, 2 Drawing Sheets

SWAB DISPENSER WITH FLUID RESERVOIR

CROSS-REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to arts and crafts, medical, electronic, and health and beauty products, more particularly, to a device for storing swabs and a wetting fluid.

2. Description of the Related Art

Cotton swabs are handy tools for applying fluids to small areas, for example, rubbing alcohol, nail polish remover, or paint. The swabs are stored in one container and the application fluid is stored in a separate covered container. The user removes a swab from its container, removes the cap from the fluid container, wets the swab by dipping it into the fluid, and then replaces the cap. In most cases, the fluid container is substantially deeper than the length of the swab, so the container must be tilted to wet the swab, requiring two hands. Having to manipulate the swab, cap, and fluid container can be awkward and prone to accidents, particularly when putting the cap back on the fluid container while holding a wet swab. There is also the convenience factor of having to deal with two containers which may or may not be stored together.

Several solutions to the problem have been posed. For example, in U.S. Pat. No. 3,146,806, the fluid container is fitted with a stopper through which a swab can be pushed for wetting. Although this device substantially reduces the risk of accidental spillage, it does not alleviate the inconvenience of having two separate containers.

A different solution is suggested by U.S. Pat. No. 4,747,719. In this patent, the fluid is stored in hollow in the handle of the swab. When wetting is desired, the user pushes the swab onto a pin to prick a hole in the hollow, allowing the fluid to escape and wet the swab. The shortcomings of this device are that it is a one-use-only device that is relatively complicated and expensive to produce. Also, both the swab and the swab container with the pin need to be disposed of after use, no part of the device is reusable. Finally, it is not particularly cost-effective for home use.

A third solution is suggested by U.S. Pat. No. 5,378,226. In this patent, the swab is stored in a sealed bag with a smaller burst pouch that holds the fluid. The pouch is burst open while the bag is sealed, and the fluid from the pouch wets the swab within the bag. Then the bag is opened and the swab is removed. Like with the '719 patent above, this is a one-use-only device that is relatively complicated and expensive to produce. The '226 patent does disclose that there may be more than one swab in the bag. They are all wetted at the same time and must either be used or disposed of. Also like the '719 patent, all components of the device need to be disposed of after use, no part of the device is reusable. Finally, this device is not particularly convenient or cost-effective for home use.

Thus there continues to be a need for a device to safely and conveniently store swabs and wetting fluid.

BRIEF SUMMARY OF THE INVENTION

An object of the present invention is to provide a swab dispenser with an integral fluid reservoir for safely and conveniently storing swabs and a wetting fluid.

Another object is to provide a swab dispenser that is cost-effective for home, commercial, industrial use.

A further object is to provide a swab dispenser that only requires one hand to remove and wet a swab.

The present invention is a swab dispenser adapted for use with a swab that has a relatively straight, rigid handle with an absorbent material attached at an end thereof. The dispenser has a storage bin for swabs and a reservoir for a wetting fluid. The storage bin is an open top compartment that is optionally separated into compartments. The swabs stand generally vertically.

The reservoir holds a fluid for wetting the swab, so the walls of the reservoir must be impervious to the fluid. The only opening to the reservoir is an aperture in the ceiling at the low point of a depression in the ceiling. The depression causes the fluid to flow down the depression surface to the aperture. The reservoir floor is concave, with the lowest point directly below the aperture so that the fluid flows to where it is most convenient for wetting the swab. Optionally, the reservoir ceiling is removable for cleaning and refilling the reservoir.

The aperture is covered by a membrane that minimizes evaporation and spillage of the fluid. The membrane has an opening through which the swab is pushed. The opening may be intersecting slits or a circular hole. Pushing the swab into the opening causes the membrane to deform inwardly and opening a hole for the swab. The membrane is composed of a material that returns the membrane to its original shape when the swab is removed from the opening.

Optionally, the swab dispenser of the present invention includes a clear cover for protecting the swabs from contamination, providing some protection against fluid spills, and further retarding evaporation.

Alternatively, the storage bin and reservoir are separate units. The storage bin has a receptacle for receiving and holding the reservoir. Optionally, there are means for securing the reservoir into the receptacle.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION OF THE INVENTION

Figure 1:
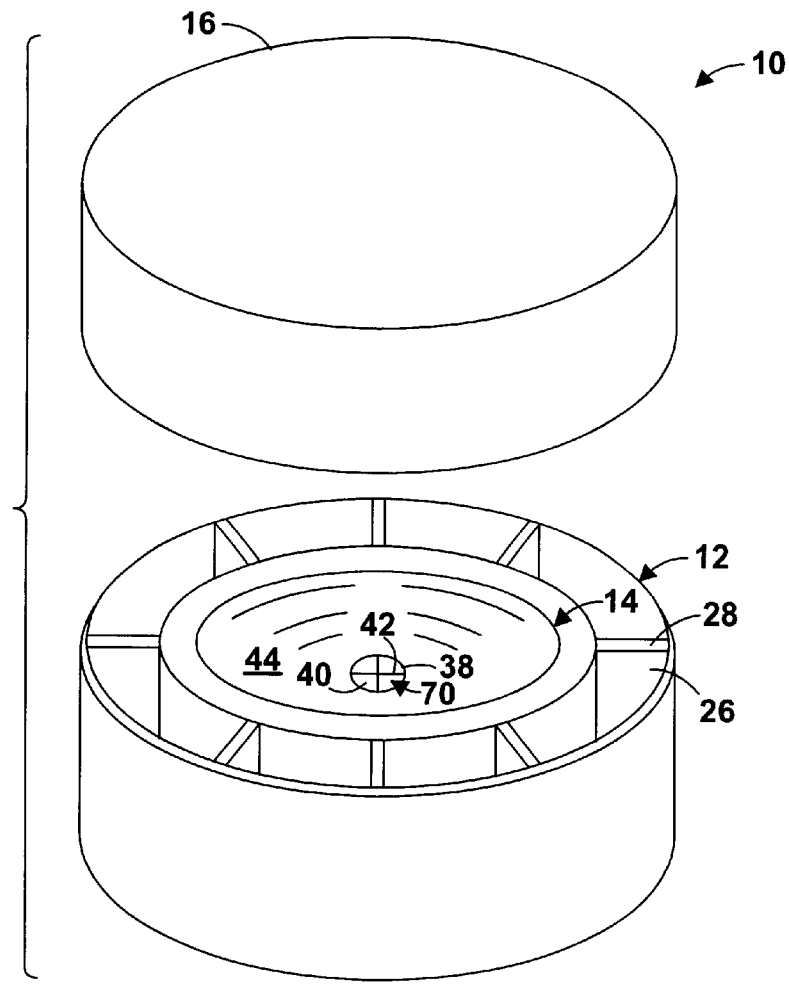
FIG. 1 is a top perspective view of the swab dispenser of the present invention.

The swab dispenser 10 of the present invention is shown in the figures. The basic dispenser 10 has a storage bin 12 for swabs and a reservoir 14 for a wetting fluid. The present invention is intended for use with swabs 20 that have a rigid handle 22 with an absorbent material 24, typically cotton, at one or both ends.

The storage bin 12 is preferably an open top compartment where the swabs 20 stand generally vertically. Optionally, the bin 12 is separated into a set of smaller compartments 26 by walls 28. The compartments 26 provides several functions. If the compartments 26 are relatively small, the swabs remain relatively vertical when there are few swabs in the bin 12 to hold each other up. If there are few swabs in the bin 12, the swabs tend to fall over. The walls 28 provide a support to hold the swabs up. More than one compartment 26 also makes it easier to separate different types of swabs so that they do not mingle and makes them easier to locate and remove.

The reservoir 14 holds a fluid 36 for wetting the swab 20 prior to use. The fluid 36 depends upon the application and may be, for example, rubbing alcohol, nail polish remover, antiseptic solutions, detergent solutions, plastic model cement, paint, or any kind of fluid that one may wish to apply with a swab. The reservoir 14 must be composed of a material that is impervious to the fluid 36. Alternatively, the inner walls of the reservoir 14 are coated with a material that renders the walls impervious to the fluid 36.

The reservoir 14 is nearly fully enclosed, with a ceiling 30, side walls 32, and floor 34. The only opening to the reservoir 14 is an aperture 38 in the ceiling 30 through which the swab 20 is pushed for wetting. The aperture 38 is preferably round, but may have any shape. The aperture 38 is at the low point of a depression 44 in the ceiling 30. The depression 44 is sloped so that most fluid 36 will flow down the depression surface 46 to the aperture 38. The preferred range of angles of slope of the depression surface 46 depends upon the intended application of the present invention 10. The more viscous the fluid 36, the steeper the angle needs to be in order for the fluid 36 to flow down the slope.

Optionally, the ceiling 30 is removable for ease in cleaning and/or refilling the reservoir 14. In such a case, the edge 54 of the ceiling 30 and the lip 52 of the reservoir 14 should provide a seal to inhibit spillage and evaporation. The seal must be impervious to the liquid held in the reservoir 14. There are a number of ways well-known in the art to accomplish this, including, but not limited to, using an O-ring between the reservoir lip 52 and ceiling edge 54 to provide a seal, and/or sizing the ceiling 30 such that it fits tightly into the reservoir lip 52, providing a compression fit seal.

The aperture 38 is preferably covered by a membrane 40 that retards evaporation and minimizes spillage of the fluid 36. The membrane 40 has an opening 70 through which the swab 20 is pushed. In one preferred embodiment, the opening 70 is composed of at least two intersecting slits 42 through which the swab 20 is pushed. When there are two slits 42, they are preferably at approximately a 90° to each other, forming an X, as in FIG. 1.

Figure 3:
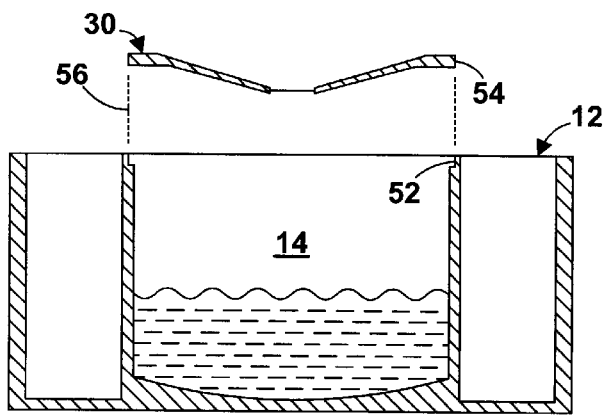
FIG. 3 is a cross-sectional view of a reservoir with a removable ceiling.
Figure 4:
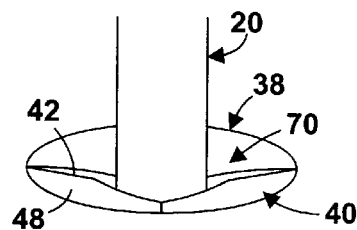
FIG. 4 is an enlarged perspective view of the membrane with slits of FIG. 1 with a swab inserted.

As a swab 20 is pushed through the slits 42, the membrane 40 deforms inwardly, as in FIG. 3, opening a hole for the swab 42. Preferably, the hole is only large enough to allow the swab 20 to fit through easily. The smaller the hole, the less evaporation and spillage of the fluid 36 there can be.

It is also preferred that the slits 42 extend across the entire aperture 38 and the membrane 40. If the aperture 38 is round, the length of the slits 42 is the same as the diameter of the aperture 38 and membrane 40. If the slits 42 are shorter than the membrane diameter, the slits 42 may tear with repeated use, increasing the size of the hole. And because the tearing will be irregular, the edges of the tear will not match, and the hole will no longer close. The present invention does contemplate that the membrane 40 may be larger than the slits 42, provided that the membrane 40 is composed of a material that resists tearing with repeated use.

The membrane 40 is composed of a material that is resilient so that it deforms inwardly when pushed by the swab 20, and is rigid enough so that it returns to its original state to cover the aperture 38 to retard evaporation when the swab 20 is removed. Preferably, the membrane 40 is composed of a rubber or plastic material.

Figure 5:
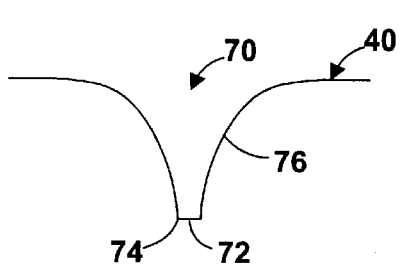
FIG. 5 is a cross-sectional view of the membrane with an approximately conic hole.

In another embodiment, the opening 70 is a small circular hole 72 in the membrane. The size of the hole 72 depends upon the elasticity of the membrane 40. In addition, as shown in FIG. 5, the membrane 40 may have an approximately conic shape in the vicinity of the hole 72, that is, the rim 74 extends away from the plane of the membrane 40 as the approximately conic section 76 decreases in diameter toward the rim 74. This or a similar structure can provide better evaporation and spillage prevention than a simple hole.

As indicated above, one use of the membrane 40 is to reduce evaporation and spillage. Another possible use is to wipe excess fluid 36 from the swab 20 as it is pulled from the reservoir 14. As a swab 20 is pushed through the slits 42, the membrane sections 48 deform inwardly. As the swab 20 is pulled from the reservoir 14, the membrane sections 48 tend to deform outwardly. As the absorbent material 24 of the swab 20 passes the membrane sections 48, pressure from the membrane sections 48 against the absorbent material 24 squeezes off fluid that would most likely drip off the swab 20 prior to use.

Preferably, the floor 34 of the reservoir 14 is concave, with the lowest point directly below the aperture 38. With a flat floor, as the level of the fluid falls, the user typically needs to tilt the reservoir to wet the swab. The concave floor 34 of the present invention eliminates the need to tilt the reservoir 14 by using gravity to cause the remaining fluid 36 to pool at the lowest point under the aperture 38, where the fluid 36 is easiest to reach.

The figures show a circular reservoir 14 in the center of the circular bin 12. This arrangement is merely illustrative. Any arrangement of the bin 12 and reservoir 14 is contemplated by the present invention.

The present invention contemplates that the dispenser 10 may be manufactured and sold with the reservoir 14 already filled with a fluid and/or that the reservoir 14 may be refilled from another container. The reservoir 14 would be refilled through the aperture membrane 40, or by removing the ceiling 30 and filling the reservoir 14 directly.

Optionally, the swab dispenser 10 of the present invention includes a cover 16. The cover 16 fits in a lip 50 on the outer wall of the storage bin 12. The cover 16 provides several advantages. It protects the swabs 20 from contamination, provides some protection against fluid spills if the dispenser 10 should be knocked over or dropped, and further retards evaporation of the fluid 36. Preferably, the cover 16 is clear so that the swabs 20 are visible.

Figure 2:
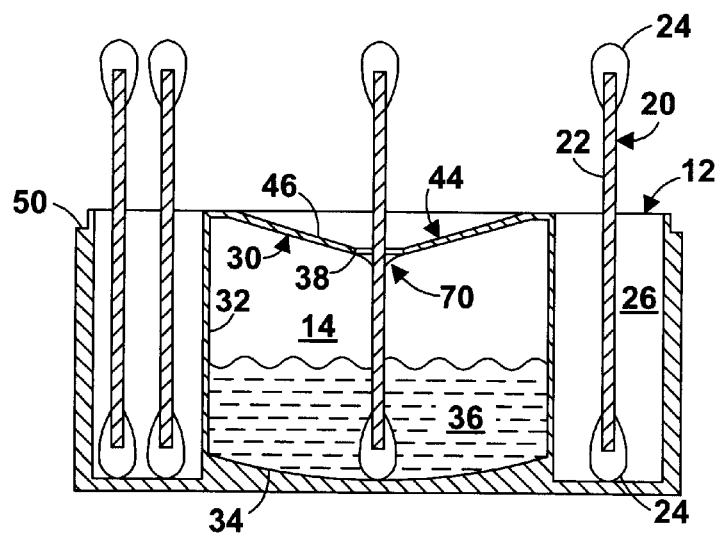
FIG. 2 is a cross-sectional view of the first embodiment of the swab dispenser of FIG. 1.
Figure 6:
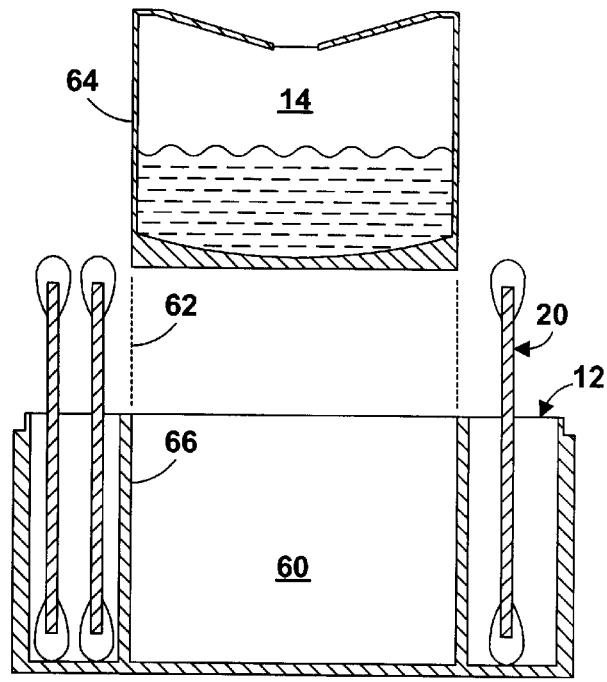
FIG. 6 is a cross-sectional view of a second embodiment of the swab dispenser of FIG. 1.

An alternative embodiment of the present invention is shown in FIG. 6. In the embodiment of FIG. 2, the storage bin 12 and reservoir 14 are a unit, that is, they are not separable. In the embodiment of FIG. 5, the storage bin 16 and reservoir 14 are separate units. The storage bin 12 includes a receptacle 60 into which the reservoir 14 is installed, as at 62. The advantage of this embodiment is that one or the other of the storage bin 12 and reservoir 14 can be discarded when empty and replaced by a filled bin 12 or reservoir 14, rather than discarding the entire dispenser 10. Optionally, the storage bin 12 can include a means for securing the reservoir 14 into the receptacle 60. Such means could include, for example, a snug fit between the outer wall 64 of the reservoir 14 and wall 66 of the receptacle 60. Other examples include hooks, mating microcatch patches, and mild adhesives.

Thus it has been shown and described a swab dispenser with an integral fluid reservoir which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A swab dispenser adapted for use with a plurality of swabs, each of said swabs having a relatively straight, rigid handle with an absorbent material attached at an end thereof, said dispenser comprising:
   (a) a bin adapted to store said swabs;
   (b) a fluid reservoir having a removable ceiling, said removable ceiling providing a seal with said fluid reservoir to substantially inhibit spillage and evaporation, said ceiling having an outer surface with a depression with a low point;
   (c) an aperture in said ceiling at said low point of said depression; and
   (d) a membrane covering said aperture, said membrane having an opening means adapted to allow said swab to be inserted through said membrane into said reservoir, said opening means substantially inhibiting spillage and evaporation when said swab is not inserted through said membrane.

2. The swab dispenser of claim 1 wherein said opening means includes at least two intersecting slits adapted to allow each one of said swabs to be inserted through said slits into said reservoir by temporarily deforming said membrane.

3. The swab dispenser of claim 2 wherein said slits extend completely across said aperture.

4. The swab dispenser of claim 2 wherein there are two of said slits forming an approximately 90° angle to each other.

5. The swab dispenser of claim 1 wherein said opening means includes a circular hole adapted to allow each one of said swabs to be inserted through said hole into said reservoir by temporarily deforming said membrane.

6. The swab dispenser of claim 1 wherein said reservoir has a concave floor with a low point located approximately under said opening means.

7. The swab dispenser of claim 1 wherein said swab dispenser further comprises a removable cover.

8. The swab dispenser of claim 1 wherein said bin has walls dividing said bin into a plurality of compartments.

9. The swab dispenser of claim 1 wherein said bin stores said swabs approximately vertically.

10. A swab dispenser adapted for use with a plurality of swabs, each of said swabs having a relatively straight, rigid handle with an absorbent material attached at an end thereof, said dispenser comprising:
    (a) a bin having at least one compartment adapted to store said swabs, said bin having a receptacle;
    (b) a fluid reservoir in said receptacle and being removable from said receptacle;
    (c) said fluid reservoir having a ceiling, said ceiling having an outer surface with a depression with a low point;
    (d) an aperture in said ceiling at said low point of said depression; and
    (e) a membrane covering said aperture, said membrane having an opening means adapted to allow said swab to be inserted through said membrane into said reservoir, said opening means substantially inhibiting spillage and evaporation when said swab is not inserted through said membrane.

11. The swab dispenser of claim 10 wherein said opening means includes at least two intersecting slits adapted to allow each one of said swabs to be inserted through said slits into said reservoir by temporarily deforming said membrane.

12. The swab dispenser of claim 11 wherein said slits extend completely across said aperture.

13. The swab dispenser of claim 11 wherein there are two of said slits forming an approximately 90° angle to each other.

14. The swab dispenser of claim 10 wherein said opening means includes a circular hole adapted to allow each one of said swabs to be inserted through said hole into said reservoir by temporarily deforming said membrane.

15. The swab dispenser of claim 10 wherein said reservoir has a concave floor with a low point located approximately under said opening means.

16. The swab dispenser of claim 10 wherein said swab dispenser further comprises a removable cover.

17. The swab dispenser of claim 10 wherein said bin has walls dividing said at least one compartment into a plurality of compartments.

18. The swab dispenser of claim 10 wherein said bin stores said swabs approximately vertically.

* * * * *